United States Patent

Takazawa et al.

Patent Number: 5,824,552
Date of Patent: Oct. 20, 1998

[54] MEDIUM FOR CULTURING ANIMAL CELLS

[75] Inventors: Yoshiharu Takazawa; Takami Arai; Masamichi Motoki, all of Hino; Kenji Nagura, Iwakuni; Seiichi Yokoyama, Tokyo; Yoshinobu Miyatsu, Kumamoto; Hiroshi Mizokami, Koushi-machi, all of Japan

[73] Assignees: Teijin Limited; Juridical Foundation The Chemo-Sero-Therapeutic Research Institute, both of Japan

[21] Appl. No.: 693,291

[22] PCT Filed: Jan. 30, 1995

[86] PCT No.: PCT/JP95/00113

§ 371 Date: Aug. 15, 1996

§ 102(e) Date: Aug. 15, 1996

[87] PCT Pub. No.: WO95/22599

PCT Pub. Date: Aug. 24, 1995

[30] Foreign Application Priority Data

Feb. 18, 1994 [JP] Japan .................................. 6-021248

[51] Int. Cl.$^6$ ...................................... C12N 5/00
[52] U.S. Cl. ...................... 435/384; 435/369; 435/325; 435/70.3; 435/70.1; 435/41
[58] Field of Search .......................... 435/41, 70.1, 70.3, 435/325, 369, 384

[56] References Cited

U.S. PATENT DOCUMENTS 4,657,866 4/1987 Kumar ..................................... 435/240

FOREIGN PATENT DOCUMENTS

| 283 942 | 3/1987 | European Pat. Off. . |
|---|---|---|
| 58-63385 | 4/1983 | Japan . |
| 267269 | 11/1988 | Japan . |
| 1-291796 | 11/1989 | Japan . |
| 4-131091 | 5/1992 | Japan . |
| 93/22448 | 11/1993 | WIPO . |

OTHER PUBLICATIONS

Ohashi, et al. 1984. PNAS, vol. 81, pp. 7132–7136.
Pace, et al. 1967, Canadian Journal of Biochemistry, vol. 45 pp. 81–88.

*Primary Examiner*—Nancy Degen
*Assistant Examiner*—Matthew Latimer
*Attorney, Agent, or Firm*—Wenderoth, Lind & Ponack

[57] ABSTRACT

A method is disclosed for culturing animal cells in a medium characterized in that said medium contains a compound represented by the general formula

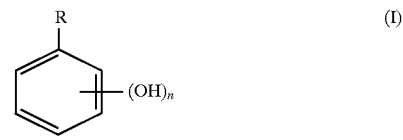

wherein, R denotes COOM or CHO, herein M denotes hydrogen, an alkali metal or a $C_1$ to $C_3$ alkyl group, and n is an integer of 1 to 3.

According to the present method, proliferation of animal cells can be enhanced with good reproducibility.

14 Claims, 10 Drawing Sheets

FIG. 9
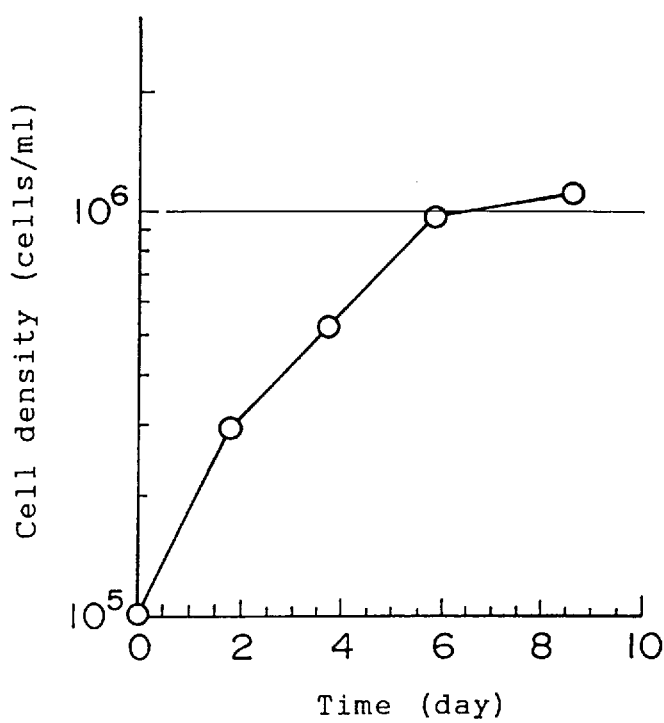
(a)
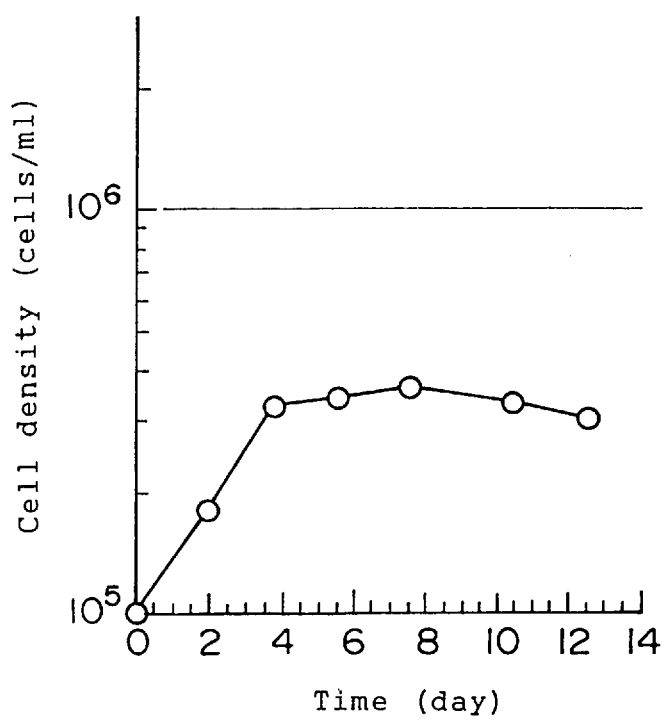
(b)

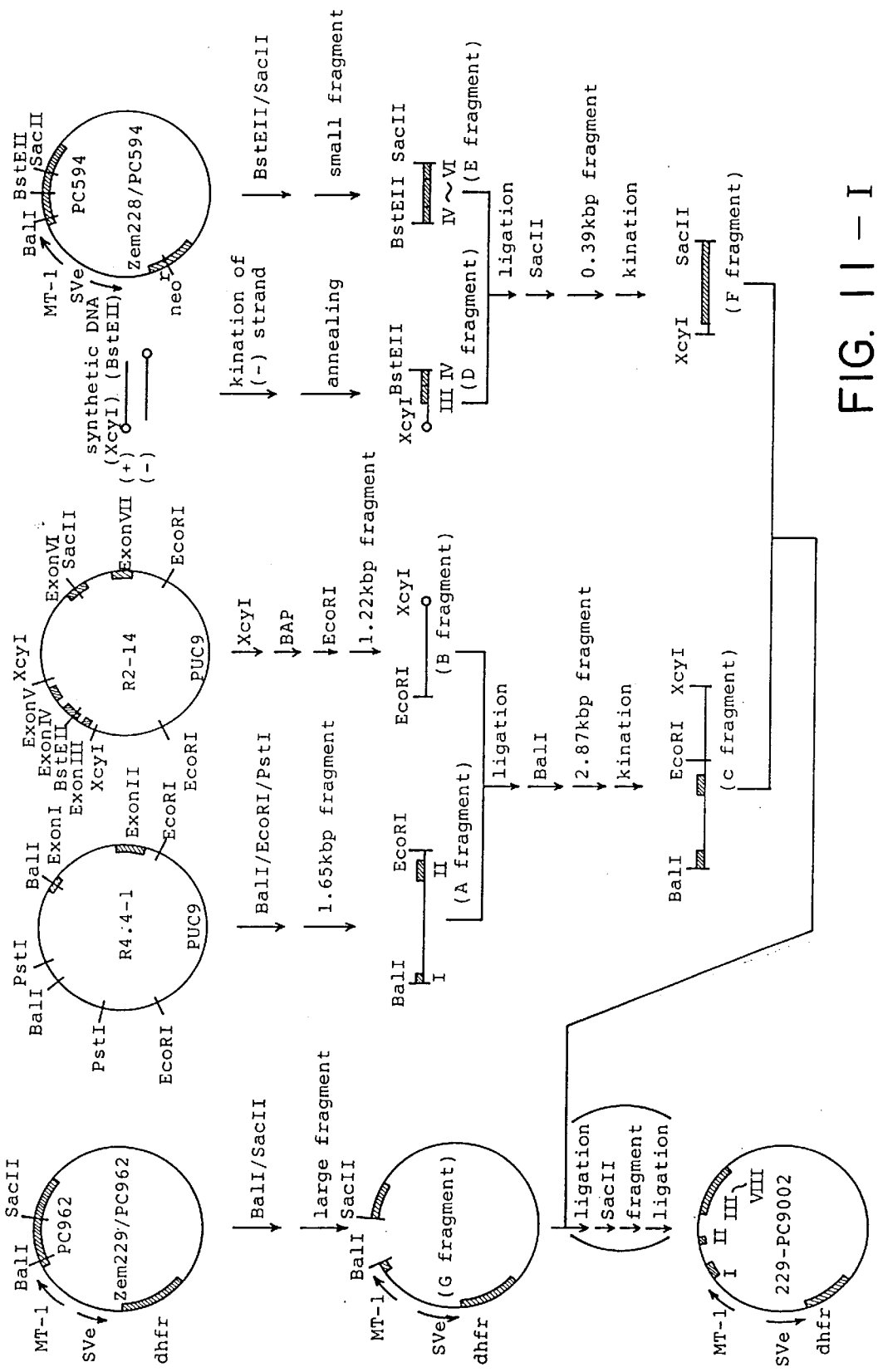
FIG. 11-I

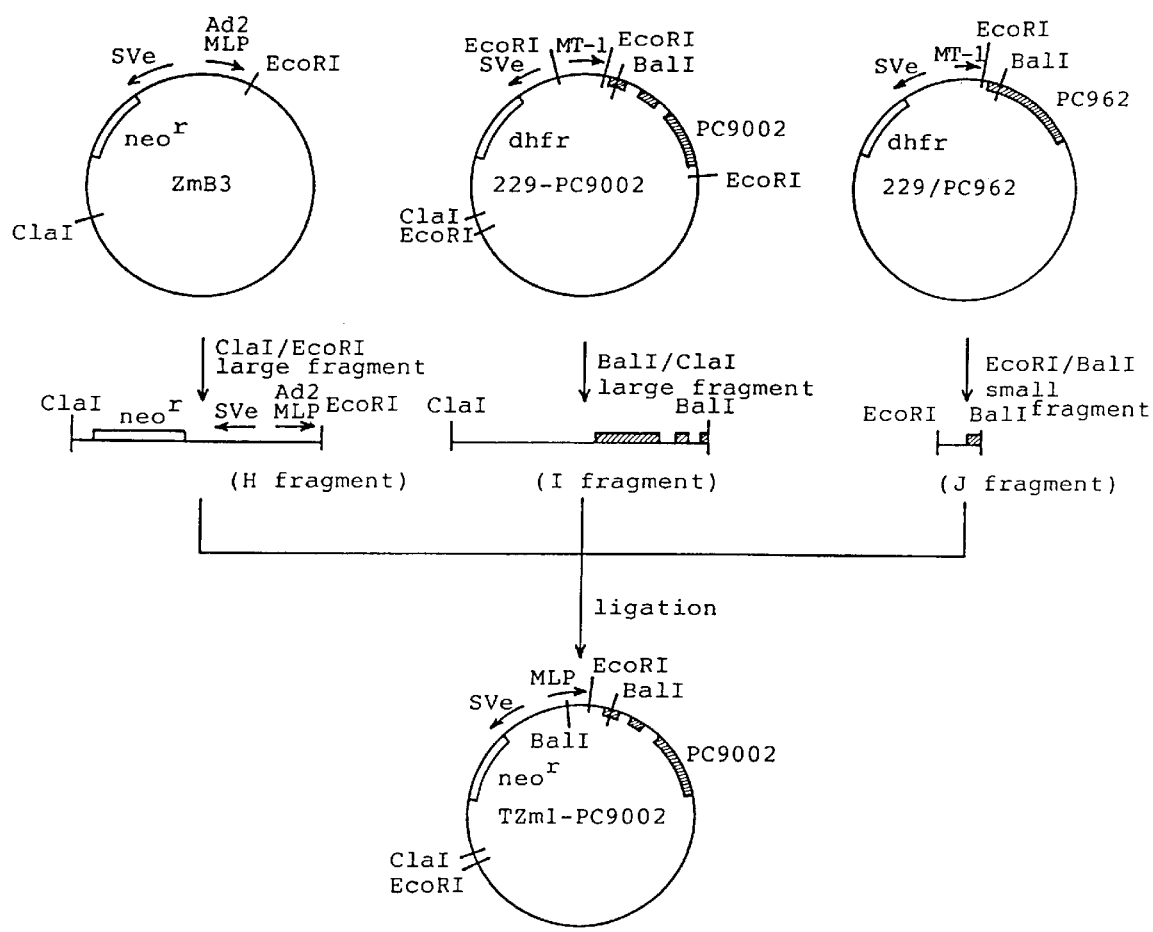
FIG. 11 - II

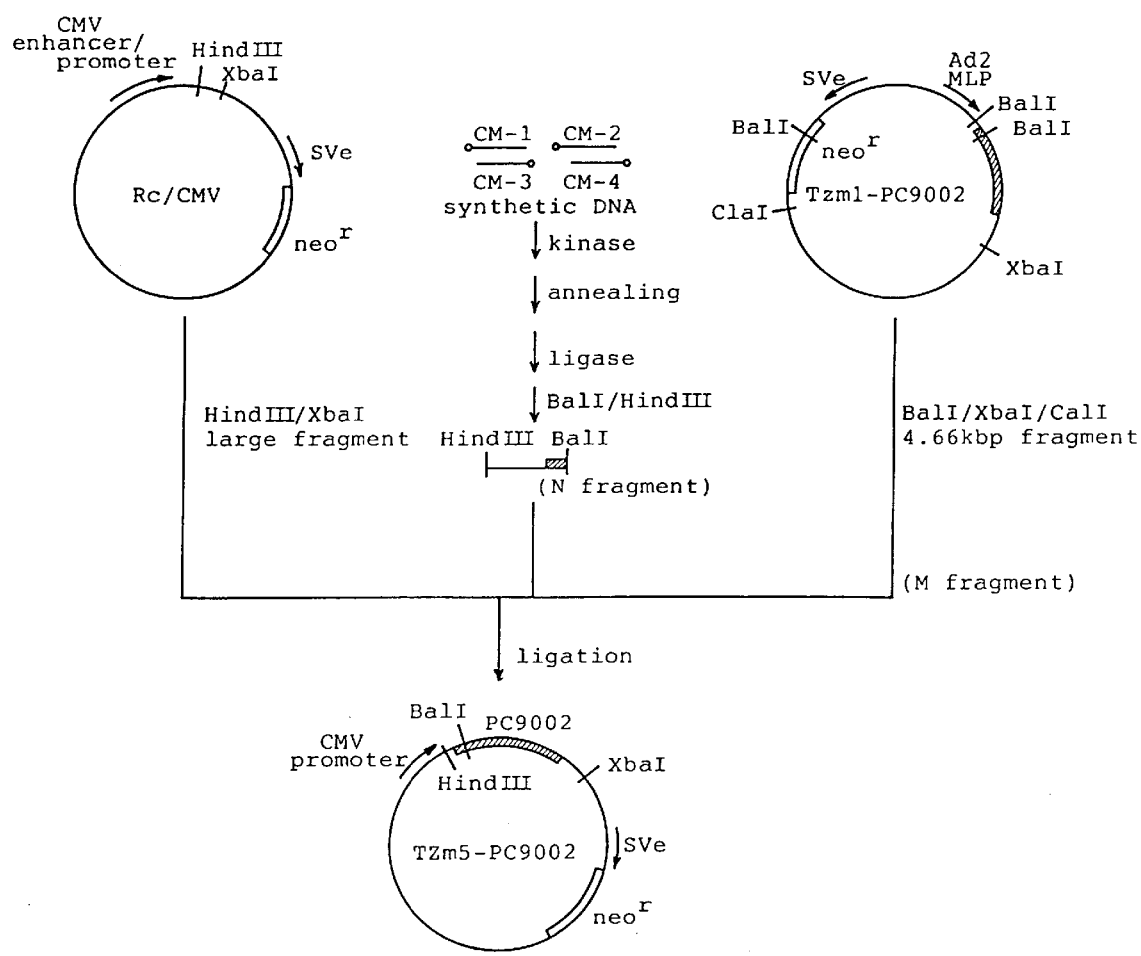
FIG. 11 - III

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( v ) FRAGMENT TYPE:

( v i ) ORIGINAL SOURCE:
        ( A ) ORGANISM: Homosapiens ( x i ) SEQUENCE DESCRIPTION: SEQ ID NO:1:

```
AGCTTGGGGC  TGTCGCGGCA  GGACGGCGAA  CTTGCAGTAT  CTCCACGACC        50
```

( 2 ) INFORMATION FOR SEQ ID NO:2:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( v ) FRAGMENT TYPE:

( v i ) ORIGINAL SOURCE:
        ( A ) ORGANISM: Homosapiens ( x i ) SEQUENCE DESCRIPTION: SEQ ID NO:2:

```
CGCCCCTGTG  CCAGTGCCTC  CAGAATGTGG  CAGCTCACAA  GCCTCCTGCT          50

GTTCGTGG                                                            58
```

( 2 ) INFORMATION FOR SEQ ID NO:3:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( v ) FRAGMENT TYPE:

( v i ) ORIGINAL SOURCE:
        ( A ) ORGANISM: Homosapiens ( x i ) SEQUENCE DESCRIPTION: SEQ ID NO:3:

```
ACCCCGACAG  CGCCGTCCTG  CCGCTTGAAC  GTCATAGAGG  TGCTGGGCGG          50

GGACAC                                                              56
```

( 2 ) INFORMATION FOR SEQ ID NO:4:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( v ) FRAGMENT TYPE:

( v i ) ORIGINAL SOURCE:
        ( A ) ORGANISM: Homosapiens ( x i ) SEQUENCE DESCRIPTION: SEQ ID NO:4:

```
GGTCACGGAG  GTCTTACACC  GTCGAGTGTT  CGGAGGACGA  CAAGCACC            48
```

MEDIUM FOR CULTURING ANIMAL CELLS

This is the national stage of PCT/JP95/00113, filed Jan. 30, 1995.

DESCRIPTION

1. Technical Field

This invention relates to a method of culturing animal cells, and more specifically relates to a method of culturing animal cells whereby proliferation of the animal cells is enhanced and the yield of the cell itself or an useful substance produced thereby is increased, and at the same time wherein reproducibility is remarkably improved.

2. Background of the Art

Culture of animal cells is now an inevitable technique for production of various physiologically active substances, construction of drug assay systems, analysis of cell functions, etc. In culture of animal cells, is generally used a serum medium comprising a medium having added thereinto bovine serum, etc., or a so-called serum-free medium comprising a medium having added thereinto growth factors such as hormones. However, some cells do not sufficiently proliferate even by addition of a serum or addition of growth factors generally used. Therefore, it is useful to search for substances having a further growth enhancement action on these cells.

Heretofore, many substances have been reported as exhibiting a growth enhancement action on various cells, but many of them are peptides and expensive. Although it is advantageous if there are inexpensive low molecular compounds exhibiting an animal cell growth enhancement action, there are only a few reports thereon. For example, a serum-free medium or low serum medium containing p-aminobenzoic acid is disclosed as an example of media for culture of hybridomas or human or animal cell lines in Japanese Laid-Open Patent Publication No. 63385/1983 and U.S. Pat. No. 4,657,866. However, so long as we carried out an animal cell culture test in a medium containing p-aminobenzoic acid, an animal cell growth enhancement effect could not be obtained.

Further, it is disclosed in Japanese Laid-Open Patent Publication No. 291796/1989 that, in production of human tissue plasminogen activator (tPA) by adherent cells, it is effective for increase of the productivity of single-strand tPA and prevention of detachment of the cells from the vessel wall or beads to add a p-aminomethyl benzoate in the medium.

On the other hand, it is disclosed in the WO93/22448 pamphlet subjected to International Publication on Nov. 11, 1993 that a culture broth where a useful protein was accumulated in a high concentration was obtained by culturing a human fetal nephric cell-derived 293 strain, in which a gene expressing the useful protein was introduced, in a medium comprising an e-RDF medium comprising a mixture of RPMI 1160 Medium, Ham's F-12 Medium and DULBECCO modified Eagle's Medium in 2:1:1 having added amino acids, glucose, etc. thereto, having added to the e-RDF medium insulin, transferrin, ethanolamine and sodium selenite as growth factors. However, when the example of the above WO93/22448 was checked, there could not be obtained any culture broth where the useful protein was accumulated in such a high concentration as described in the example, although the reason is not clear.

The main object of this invention is to provide low molecular compounds for addition to media for culture of animal cells, which can express, with reproducibility, an animal cell growth enhancement action.

Another object of this invention is to provide a method of proliferating animal cells or increasing the yield of a useful substance produced thereby, with reproducibility, by culturing the animal cells in a medium containing such a low molecular weight compound.

Other objects and characteristics of this invention will be apparent from the following description.

DISCLOSURE OF INVENTION

This invention provides a method of culturing animal cells in a medium characterized in that said medium contains a compound represented by the general formula:

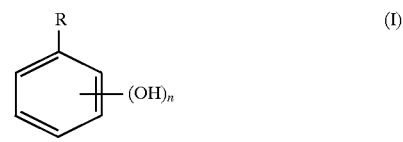

wherein, R denotes COOM or CHO, herein M denotes hydrogen, an alkali metal or a $C_1$ to $C_3$ alkyl group, and n is an integer of 1 to 3.

According to this invention is further provided a medium composition for animal cells containing nutrients necessary for proliferation of the animal cell and a compound of the above formula (I).

This invention is further detailedly described below.

The most characteristic point of this invention lies in using a benzoic acid or benzaldehyde derivative represented by the above formula (I) as an animal cell growth-enhancing agent in culture of the animal cell. In the formula (I), the alkali metal (M) includes lithium, potassium, sodium, etc., and the $C_1$ to $C_3$ alkyl group (M) includes methyl, ethyl, propyl and isopropyl groups.

Specific examples of compounds of the formula (I) include, for example the following ones:

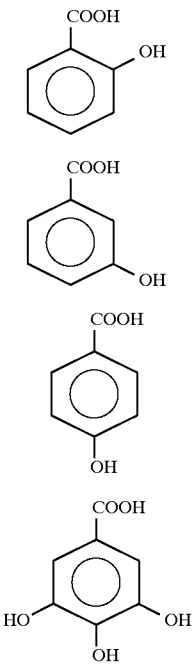

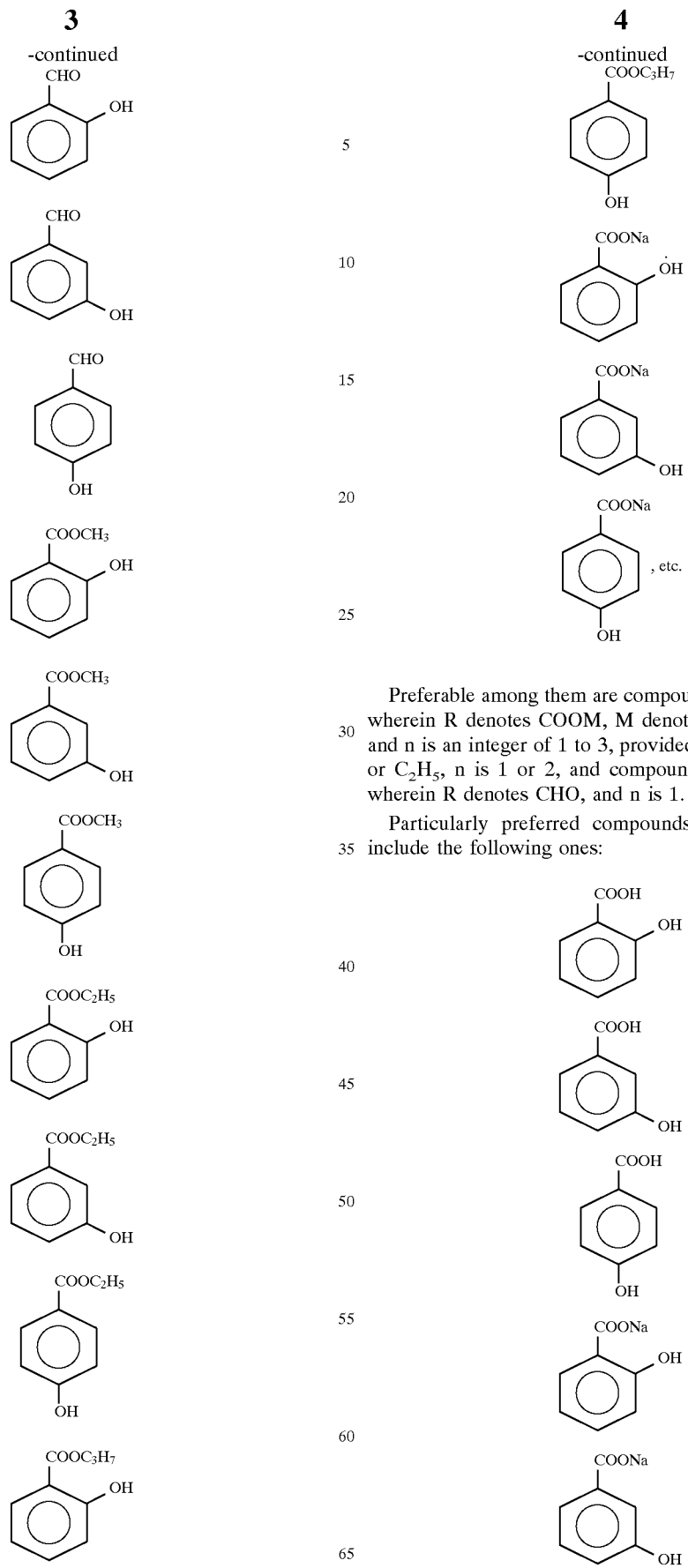
Preferable among them are compounds of the formula (I) wherein R denotes COOM, M denotes Na, $CH_3$ or $C_2H_5$, and n is an integer of 1 to 3, provided that when M is $CH_3$ or $C_2H_5$, n is 1 or 2, and compounds of the formula (I) wherein R denotes CHO, and n is 1.
Particularly preferred compounds of the formula (I) include the following ones:

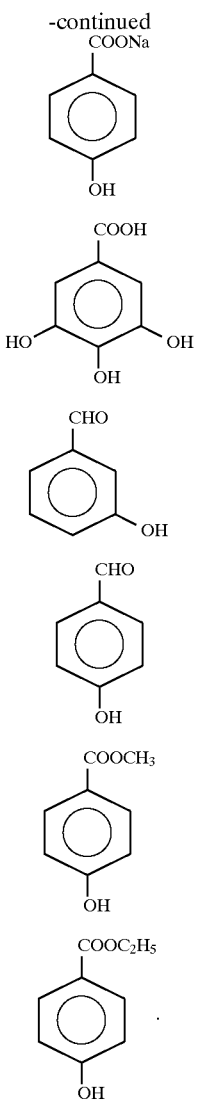

The concentration of a compound of the above formula (I) in the medium is not strictly limited, and can be varied over a wide range depending on the composition and culture conditions of the medium used, the kind of the animal cell, etc., but the concentration can be within the range of generally 0.05 to 50 μg/ml, preferably 0.2 to 20 μg/ml, more preferably 1 to 10 μg/ml.

The compound of the formula (I) is substantially not consumed by the animal cell during culture, and therefore, in the case of batch culture or fed-batch culture, when the compound is first added within the above range of concentration, it is unnecessary to additionally add it later, but it is possible to add it supplementarily, if desired. On the other hand, in the case of perfusion culture, it is desirable to add a compound of the formula (I) continuously or intermittently to the medium so that the concentration within the above range is substantially maintained during the culture.

The way of addition of the compound of the formula (I) to the medium is not particularly limited, but it is convenient to add one being water soluble as an aqueous solution and one being sparingly soluble in water in such a form that it is dissolved in a mixed solvent of water with a water-miscible organic solvent having low toxicity on animal cells, e.g. ethanol.

As to animal cells which can be cultured according to the method of this invention, there is no particular limitation so long as they can be cultured, in vitro, in suitable media, and they can be established ones or unestablished ones, or they can also be transformed by genetic technique, or they can further also be hybridomas. Such animal cells, particularly mammalian cells include, for example, tumor cells, fetus-derived cells, various established animal cells, antibody-producing hybridomas, etc, and more specifically, include, for example, as those available from American Type Culture Collection, Maryland, U.S.A., HeLa (derived from human neck of uterus, ATCC CCL 2), Hep G 2 (derived from human hepatoma, ATCC HB 8065), 293 strain (derived from human fetal kidney, ATCC CRL 1573), BHK-21 (C-13), BHK-21C-13 (derived from hamster kidney, ATCC CCL 10 and CRL 8544), CHO 1-15$_{500}$, CHO-1C6, CHO/dhFr, CHO-K1 (derived from Chinese hamster ovary, ATCC CRL 9606, CRL 1793, CRL 9096, CCL 61 and CRL 9618), etc. However, these are mere examples, and animal cells usable in this invention are not limited thereto. These cells can, if desired, be transformants wherein genes encoding useful physiologically active substances are introduced so as to be expressable.

Further as an antibody-producing hybridoma, there can be mentioned one obtained by cell fusion of a mammalian B cell with a mammalian myeloma cell.

As to media for culturing these animal cells, there is no particular limitation so long as they contain nutrients necessary for growth of the animal cells, and an optimum medium can be selected and used in accordance with the animal cell to be cultured. Examples of such media include, as basal media, commercial media such as, for example, MEM, α-MEM, DMEM, Fisher's Medium, Ham's F-12 Medium, RPMI 1640 Medium and e-RDF; serum media comprising these basal media having added thereto sera,; and so-called serum-free media comprising these basal media having added thereto growth factors such as insulin, transferrin, ethanolamine and sodium selenite, in place of sera.

Particularly suitable is a medium rich in glucose wherein glucose is added in a concentration of 2,000 to 5,000 mg/l.

Culture of animal cells in such a medium can be carried out using a method known per se, except for using a medium wherein a compound of the above formula (I) is added in such a concentration as mentioned above. For example, the culture can be carried out by static culture, suspension culture or other methods. Herein, suspension culture is a method wherein cells are cultured while the cells are suspended by itself or in a state of being carried on a carrier such as a microcarrier.

Culture can be carried out according to any of batch culture, fed-batch culture and continuous culture such as perfusion culture.

As to oxygen concentration in the culture broth, concentration known per se in the field of animal cell culture technique can be adopted in general, and the concentration can basically be such a concentration that the animal cell can live, but is preferably a sufficient concentration. The effect of this invention tends to show itself more clearly in suspension culture where controling the oxygen concentration is easier, than in static culture where the controling is difficult in general. It is preferable to adjust the oxygen concentration in suspension culture generally within 1 to 5 ppm, particularly to around 3 ppm. However, it is not meant that the effect of this invention is not observed at concentrations lower than that.

As an example of methods of obtaining useful proteins by culturing animal cells, utilizing the foregoing process of this invention, there can be provided, according to this invention, a method for obtaining a useful protein by culturing protein-producing animal cells in a medium, recovering the produced protein from the culture broth, and, if necessary, further treating the protein, characterized in that said medium contains a compound of the above formula (I), and the protein-producing animal cell line is an animal cell line transfected with an expression recombinant vector containing a gene encoding a Gla protein, for example 293 strain derived from the human fetal kidney which is trasfected with Gla protein gene.

As to the above Gla proteins, various ones are known, and proteins which are naturally γ-carboxylated, appropriately folded, and subjected to processing are included. For example, there can be mentioned human protein C or activated human protein C, factor VII, factor IX, factor V, protein S, protein Z, prothrombin, etc.

Genes encoding these are also known, and, for example, a gene encoding human protein C or activated human protein C is described in U.S. Pat. No. 4,775,624 and U.S. Pat. No. 4,968,626.

As to expression recombinant vectors containing these genes, various ones are already reported, and, for example, as to human protein C or activated human protein C, various vectors are described in U.S. Pat. No. 4,992,373, EP 0 323 149 A2, EP 0 245 949 A2, EP 0 363 127 A2, U.S. Pat. No. 4,959,318, EP 0 319 944 A2 and WO92-13079, etc., in addition to the above two U.S. patents.

Any of these known vectors can be used as the expression vector in this invention.

As to methods of transforming animal cells using these expression vectors to give desired protein-producing animal cells, methods known per se can be applied as such.

Animal cells transfected with the above expression vectors are not particularly limited, and include, for example, CHO cell, BHK cell, 293 cell, AV12 cell, etc. Among them, a human fetal kidney cell line-derived cell comprising a human kidney cell having been transformed with an adenovirus expressing an EIA gene product, for example 293 cell (ATCC CRL-15753) is particularly fit for use in this invention, since when cultured in the presence of vitamin K after being transformed so as to express a Gla protein, the cell can appropriately γ-carboxylate a complicated gene product such as protein C or activated protein C, and can further accurately make processing of the product.

Further, a syrian hamster cell line AV12-664 (hereafter, sometimes abbreviated as AV12) is also one of animal cell lines preferable for the purpose of producing γ-carboxylated proteins.

By culturing an animal cell line transfected with an expression vector, thus obtained, a Gla protein, for example protein C or activated protein C can be produced in the culture broth.

As methods for purifying and recovering the protein from such culture broth, there can be used methods which have so far been known. For example, as to methods using antibody columns, by applying antibodies and purification methods described in EP 0 205 046 B1 and EP 0 287 028 B1, a person skilled in the art can readily carry out the purification and recovery. A method using an ion exchange resin, in place of using an antibody, can also be used, and, for example a method described in U.S. Pat. No. 4,981,952 can be mentioned.

When proteins secreted by the above animal cells are final substances, final products are obtained by the above purification methods, but when proteins secreted are substances as precursors, it is necessary to further convert them into final substances before or after the above purification.

For example when the above secreted protein is protein C, it can itself be a final substance usable for therapy use, but, more preferably, it can be converted into activated protein C by cleaving and removing the activation peptide. Such activation methods are techniques well-known by a person skilled in the art, and can readily be carried out using enzymes such as, for example, thrombin, thrombin-thrombomodulin complex, trypsin and venom (see, U.S. Pat. Nos. 4,775,624 and 4,968,626).

When the thus formed activated protein C is purified, the above method using an antibody or the above method using an ion exchange resin can be used alone or in combination.

According to the foregoing method of this invention using the compound of the above formula (I), various excellent effects as mentioned below are obtained:

1. Proliferation of an animal cell can be enhanced.
2. When the animal cell has a useful protein-producing ability, the protein-producing ability can be enhanced.
3. The compound has an effect of stabilizing the pH of the medium, and when not particularly controlled, the pH of the medium can be maintained within the range of 6.5 to 7.5 fit for culture of animal cells.
4. The process is excellent in reproducibility, and when culture is repeated, there is no large dispersion in the growth ratio of the animal cell or the yield of the product per culture.
5. Only a small amount of harmful metabolites (e.g., lactic acid, ammonia, etc.) are accumulated in the medium, and therefore, lowering of the cell density and lowering of the growth rate are inhibited, and production of the useful substance can be maintained in high levels.

BRIEF DESCRIPTION OF DRAWINGS

FIG. 9 is a graph showing the changes with time lapse of the cell densities, obtained in Example 9 and Comparative example 4.

FIG. 11 is a schematic drawing showing a preparation procedure of vector TZm5-PC9002 according to Reference example.

REFERENCE EXAMPLE

Figure 1:
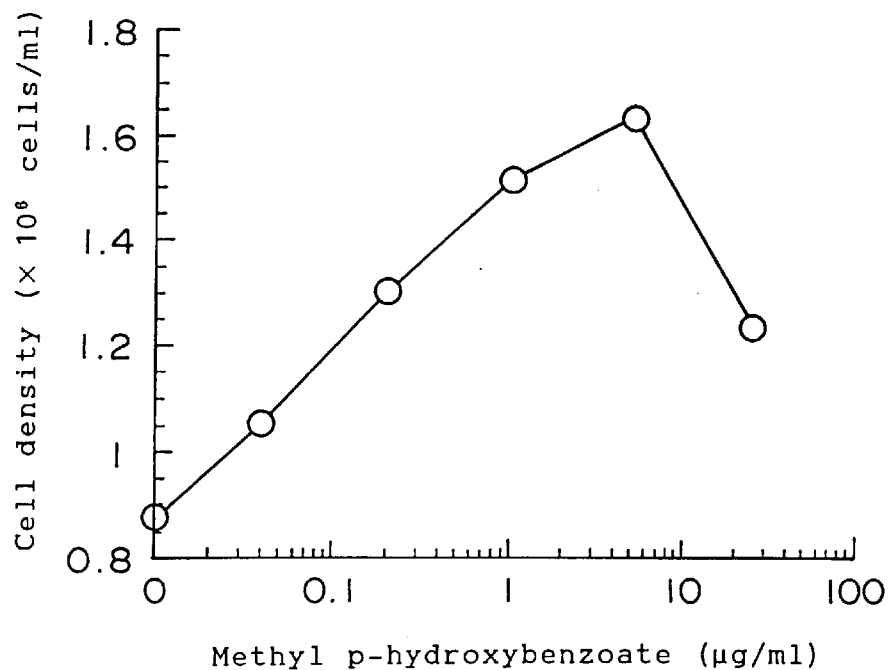
FIG. 1 is a graph showing the relation between the concentration of methyl p-hydroxybenzoate and the cell density, obtained in Example 2.

The protein C-producing cell used in this invention was prepared using the following method.

Cleavage of DNA

Cleavage of each 1 μg of plasmid DNA, or the replicative form (RF) DNA of M 13 phage or a DNA fragment thereof was carried out by using 4 to 10 units each of restriction enzymes in 10 μl of a buffer, and holding the buffer at a temperature designated by the maker for 2 hours. The buffer attached to the enzymes is used as the buffer.

Recovery of DNA Fragments From Agarose Gel

DNA fragments formed by cleavage with the restriction enzymes were separated by agarose gel electrophoresis using a submarine-type electrophoretic vessel. The agarose gel containing the desired DNA fragment was cut out, and recovered using GENECLEAN II (registered trade mark) (Bio 101 Co.). The method therefor was carried out according to the attached operating manual.

Ligation of DNA Fragments

Carried out using the DNA ligation kit (TAKARA SHUZO). The method obeyed the operating manual attached to the kit.

Blunting the Ends of DNA

Carried out using the DNA blunting kit (TAKARA SHUZO). The method obeyed the operating manual attached to the kit.

Transformation of Escherichia Coli

20 μl or less of the resultant DNA solution was added to competent cells (TAKARA SHUZO) of *Escherichia coli* HB101 strain, and the vessel was put on ice for one hour. The vessel was incubated in a water bath of 42° C. for one minute, and then put again on ice for 5 minutes. The contents were added to 1 ml of L-broth, the mixture was subjected to shaking culture for one hour, and part thereof (50 to 300 μl) was spread on an ampicillin plate (L-broth, 15 g/l agar, 50 μg/ml ampicillin) and cultured at 37° C. overnight to give colonies.

Small-Scale Preparation of Plasmid DNA

Preparation by the alkali lysis method ("Molecular Cloning" (T. Manlatia, Cold Spring Harbor Laboratory, 1982), see page 368) was carried out.

Purification by "GENECLEAN II (registered trade mark)" of Bio 101 Co. was carried out, when needed.

Large-Scale Preparation of Plasmid DNA

Carried out according to the alkali lysis method ("Transcription and Translation" (B. D. Hames, IRL press, 1984), see page 8) and the CsCl equilibrium density gradient centrifugation method. Herein, a RP-67 VF vertical rotor made by Hitachi Co. was used as the ultracentrifuging rotor. Removal of CsCl was not made by dialysis, and was carried out, in its place, by carrying out ethanol precipitation two times after 4-fold dilution with TE (10 mM Tris-HCl, pH 8.0, 0.1 mM EDTA).

DNA Base Sequencing

The DNA fragment to be base sequenced was integrated into bacteriophage M13 to give a single-strand DNA.

This method is described in the operating manual attached to "M13 Cloning Kit" from Amersham. Further, large amount preparation of the single-strand DNA was carried out according to the method described in the operating manual attached to "Oligonucleotide-directed in vitro mutagenesis system" from the same company. Sequencing reaction was carried out using the resultant single-strand DNA as a template, using as a primer 20 mer of a synthetic DNA on the vicinity of the region to be examined, prepared by the later-described method, and using "Dye Deoxy™ Terminator Taq Sequencing kit" from Applied Biosystem Co.

The sample obtained by this reaction was analyzed using a 373-type DNA sequencer from Applied Biosystem Co. to determine the base sequence.

Chemical Synthesis and Purification of the DNA Fragment

Synthesized by a 380 A-type DNA synthesis apparatus from Applied Biosystem Co. under the condition of "TrON, AUTO". The "Oligonucleotide purification cartridge" was used for its purification in accordance with the operating manual attached thereto.

The following plasmid or DNA fragment was used in preparation of the DNA fragments and expression vectors used in this invention.

pDX/PC pDX/PC is a human protein C expression vector disclosed in Foster, D. C. et al., Biochemistry 26, 7003-7011 (1987) or U.S. Pat. No. 4,968,626, and has adenovirus type II major late promoter and has full length human protein C cDNA downstream thereof.

Description is made on the functional part constituting this expression vector in Busby, S. et al., Nature, 316, 271–273 (1985) and Berkner, K. L. et al., Nuc. Acids Res., 13, 841–857 (1985).

Human protein C genomic DNA

Human protein C genomic DNA is described in U.S. Pat. No. 4,968,626.

In the DNA, the DNA fragment (hereafter referred to as R4.4-1) from the EcoRI site in the intron between Exon 2 and Exon 3 to the EcoRI site located about 4.4 kbp upstream therefrom, and the about 6.2 kbp DNA fragment (hereafter referred to as R2-14) from the EcoRI site in the intron between Exon 2 and Exon 3 to the EcoRI site in the intron between Exon 7 and Exon 8 were used, in the following procedure, after being subcloned into the EcoRI site of PUC9.

Zem228, Zem229

These expression vectors are disclosed in EP 0 319 944 A2, and the promoter of the mouse metallothionein I gene is used. Further, these expression vectors have the neomycin resistance gene and the dihydrofolate reductase gene as selective markers, respectively.

228/PC594

228/PC594 is a human protein C expression vector wherein human protein C cDNA is inserted in the BamHI site of the above Zem228. This human protein C cDNA is the same with one in the above PDX/PC.

229/PC962

229/PC962 is a modified human protein C expression vector wherein a modified human protein C cDNA PC962 is inserted in the BamHI site of the above Zem229. PC962 is shown in U.S. Pat. No. 4,959,318.

Rc/CMV

Purchased from Invitogen Co.

Creation of Human Protein C Expression Vector (1) 229-PC9002 (see, FIG. 11-I)

The above plasmid comprising PUC9 having subcloned thereinto R4.4-1 was digested with BalI, EcoRI and PstI, and an about 1.65 kbp BalI-EcoRI DNA fragment (this is referred to as Fragment A) was recovered by 0.8% agarose gel electrophoresis.

On the other hand, the above plasmid comprising PUC9 having subcloned thereinto R2-14 was digested with XcyI, dephosphorylated with alkaline phosphatase, digested with EcoRI, and then electrophoresed using 0.8% agarose gel, and an about 1.22 kbp EcoRI-XcyI DNA fragment was recovered (this is referred to as Fragment B).

A fragment obtained by ligating Fragment A to Fragment B was digested with BalI, and an about 2.87 kbp BalI-XcyI DNA fragment was recovered by 0.8% agarose gel electrophoresis, and phosphorylated with T4 polynucleotide kinase (TAKARA SHUZO) (this is referred to as Fragment C).

Further, in the sequence of the human protein C gene shown in the above U.S. Pat. No. 4,968,626 (or page 4674 of Proc. Natl. Acad. Sci. USA, 82, 1985), a sequence comprising the sequence from XcyI (the 2902nd residue) to BstEII (the 3082nd residue) having removed therefrom the intron between Exon 3 and Exon 4 was chemically synthesized.

Among both normal and reverse strands, only the DNA fragment of the reverse strand was phosphorylated with T4 polynucleotide kinase, and both strands were annealed (this is referred to as Fragment D). On the other hand, an about 0.36 kbp BstEII-SacII DNA fragment (this is referred to as Fragment E) was separated from fragments comprising the above 228/PC594 having been digested with SacII and BstEII, by 2% agarose gel electrophoresis.

A fragment obtained by ligating Fragment D to Fragment E was digested with SacII, and an about 0.45 kbp XcyI-SacII DNA fragment was recovered by 2% agarose gel electrophoresis, and phosphorylated with T4 polynucleotide kinase (this is referred to as Fragment F).

Further, from fragments comprising the above 229/PC962 having been digested with BalI and SacII, the larger fragment was recovered by 0.8% agarose gel electrophoresis (this is referred to as Fragment G). Finally, Fragment C, Fragment F and Fragment G were subjected to three-molecule ligation to give 229-PC9002. This expression vector is one for expressing a fragment comprising the human protein C gene having removed therefrom introns other than the two introns between Exon 1 and Exon 2 and between Exon 2 and Exon 3, by the mouse metallothionein I promoter, and has the transcription unit for dhfr on the same plasmid.

(2) TZm1-9002 (see FIG. 11-II)

Although the above Zem228 has two EcoRI sites, a fragment obtained by cleaving only one of the sites by partial digestion with EcoRI was recovered by agarose gel electrophoresis.

DNA polymerase I large fragment was made to act on this DNA fragment to blunt the ends of the latter fragment, and the resultant fragment was self-ligated. The resultant fragment was introduced into *Escherichia coli,* proliferated, recovered and completely digested with EcoRI, the ends of the resultant fragments were blunted again with DNA polymerase I large fragment, the resultant fragments were self-ligated, and the resultant fragments were introduced again into *Escherichia coli,* whereby this plasmid was increased. Thereby, the two EcoRI sites were disappeared.

A short double-strand synthetic DNA (adaptor) having BamHI cleavage termini at both termini and having an EcoRI site inside was inserted into the sole BamHI site in this plasmid to create an expression vector Zem 228R having an EcoRI cleavage site immediately downstream of the mouse metallothionein I promoter.

This Zem 228R was then digested with EcoRI and HindIII, and the larger fragment was recovered by agarose electrophoresis. Separately, 1.03 kbp HindIII-EcoRI fragment in the above pDX/PC was recovered, and both fragments were ligated to give ZmB-3. This expression vector has the adenovirus major late promoter together with the transcription unit for the neomycin resistance gene.

This ZmB-3 was digested with EcoRI and ClaI, and the larger fragment having the neomycin resistance gene was separated by 0.8% agarose gel electrophoresis (this is referred to as Fragment H). Further, 229-PC9002 was digested with BalI and ClaI, and the larger fragment was recovered (this is referred to as Fragment I).

Further, the above 229/PC962 was digested with EcoRI and BalI, and a small fragment was recovered by 2% agarose gel electrophoresis (this is referred to as Fragment J). Fragment H, Fragment I and Fragment J were subjected to three-molecule ligation to give TZm1-9002.

This expression vector is one for expressing a fragment comprising the human protein C gene having removed therefrom introns other than the two introns between Exon 1 and Exon 2 and between Exon 2 and Exon 3, by the adenovirus major late promoter, and has the transcription unit for the neomycin resistance gene on the same plasmid.

(3) TZm5-PC9002 (see FIG. 11-III)

The above TZ1-PC9002 was digested with BalI, XbaI and ClaI, and a 4.66 kbp DNA fragment was recovered (this is referred to as Fragment M). A DNA fragment, in human protein C cDNA, ranging from the BalI site existing 30 bp downstream from the initiation codon, to 103 bp upstream from the initiation codon, was chemically synthesized from parted two blocks. Namely, the synthesized fragment is a fragment having a Hind III cleavage site at the upstream side and a BalI cleavage site at the downstream side. The following four chemically synthesized single-strand DNAs (CM1–CM4) were phosphorylated at the 5' terminus, annealed and ligated.

CM-1 (Sequence ID No. 1)

5' AGCTTGGGGCTGTCGCGGCAGGACGGCGAA
CTTGCAGTATCTCCACGACC 3'

CM-2 (Sequence ID No. 2)

5' CGCCCCTGTGCCAGTGCCTCCAGA ATG TGG
CAGCTCACAAGCCTCCTGCTGTTC GTG G 3'

CM-3 (Sequence ID No. 3)

3' ACCCCGACAGCGCCGTCCTGCCGCTTGAAC
GTCATAGAGGTGCTGGGCGGGGACAC 5'

CM-4 (Sequence ID No. 4)

3' GGTCACGGAGGTCTTACACCGTCGAGTGTT
CGGAGGACGACAAGCACC 5'

This synthesized DNA fragment was digested with BalI and HindIII, and a 0.11 kbp DNA fragment was recovered by 2% agarose gel electrophoresis (this is referred to as Fragment N). The larger DNA fragment obtained by digesting the above Rc/CMV with HindIII and XbaI, Fragment M and Fragment N were subjected to three-molecule ligation to give TZm5-PC9002. This expression vector is one whose transcription is induced by the IE enhancer/promoter of cytomegalovirus.

Expression of Human Protein C in an Animal Cell

The 293 cell (ATCC CRL1573) was cultured in 100 ml of a medium comprising inactivated 10% FCS-eRDF (Kyokuto Seiyaku)—5 μg/ml vitamin K1 having added thereto streptomycin and penicillin G so that their concentrations could be 100 μg/ml and 100 units/ml, respectively, using a 3003 Petri dish from Falcon.

This expression vector was used in an amount of 10 μg per Petri dish. 10 μg of salmon sperm DNA and 25 μl of 2M $CaCl_2$ were added to this expression vector, and then TE (1 mM Tris HCl, 0.05 mM EDTA, pH 7.5) was added to make the total volume 200 μl.

200 μl of 2×HBS (280 mM NaCl, 50 mM HePes, 1.5 mM $NaH_2 PO_4$, pH 7.12) was added dropwise to this solution under stirring, and the mixture was allowed to stand at room temperature for 30 minutes. The medium was removed from the Petri dish where the confluency of the cell became 60% to 80%, and 3 ml of the above medium containing 100 μM of chloroquine was added.

To the mixture was added dropwise the above mixed solution containing the DNA, and the mixture was held at 37° C. for 4 hours in a 5% $CO_2$ incubator. The medium was removed, 1 ml of a glycerol solution (comprising eRDF medium having added glycerol so as to be 15%), the mixture was allowed to stand at room temperature for one minute, glycerol was removed, the cell was washed twice with 3 ml of PBS(−) (Nissui Seiyaku), 10 ml of the above medium was added, and culture was continued at 37° C. in the 5% $CO_2$ incubator.

The method stated herein is known as the calcium phosphate coprecipitation method, and shown, basically, in Wigler et al., Cell., 14, 725 (1978), and Van der Eb et al., Virology, 52, 456 (1973). On the next day, the resultant cells were peeled with trypsin, diluted 30-fold to 90-fold, and culture was continued in the above media using Falcon 3025 Petri dishes. In the meantime, 1 mg/ml portions of G418 (Gibco) were added. Thereafter, culture was carried out using these selective media.

Since colonies were formed about 18 days thereafter, they were transferred to Costar 3424 plates using a cloning cylinder. These colonies were transferred to Falcon 3003 plates, changes of liquids were carried out at the time when the cells became confluent, the cells were cultured for 24 hours, and the culture supernatants were recovered.

Then, the concentrations of the whole human protein C and the concentrations of the human protein C normally having Gla, contained in the supernatants, were assayed by the ELISA method. In this ELISA system, an anti-human protein C monoclonal antibody JTC-4 recognizing H chains was used at the plate side, and JTC-5 (recognizing the activated peptide; for assay of the whole human protein C) or JTC-1 (recognizing the Gla domain depending on Ca2+; for assay of the human protein C normally having Gla) was used as a horseradish peroxidase (HRPO)-labeled antibody.

These monoclonal antibodies are those disclosed in Wakabayashi et al., J. Biol. Chem., 261, 11097 (1986).

A colony having the maximum PC production ability in the above operations was taken out, and cloned using the limiting dilution analysis. The PC production ability of the resultant cells was checked in the same manner as described above, and a clone having 15 the maximum production ability was selected. This was designated 293 21-26 strain.

EXAMPLES

This invention is more specifically described below by examples.

Example 1

1) Medium

As a basal medium was used e-RDF Medium (as to the detailed composition, see Table III in page 580 of Nippon Nogei Kagakukaishi 58 (6), 575–583 (1984)), which comprises the 2:1:1 mixture of RPMI 1640 Medium, Fam's F12 Medium and Dulbecco's modification of Eagle's Medium, having further been supplemented with amino acids, glucose, etc., and to the e-RDF Medium were added as growth factors 9 μg/ml of insulin, 10 μg/ml of transferrin, 10 μM of ethanolamine and 20 nM of sodium selenite.

To portions of the resultant medium were added aqueous solutions or 50% ethanol solutions of additives shown in the following Table 1 (the concentration of each of the additives: 10 mg/ml), respectively, so that the concentration of each of the additives in the media could be 5 μg/ml.

2) Cell

The 293 21-26 strain, a protein C-producing strain, obtained in Reference example was used.

3) Culture method and results

Two ml portions of a $5 \times 10^4$ cells/ml suspension of the 293 21-26 strain were put in 35 mmφ plastic dishes for animal cells in which the media containing the respective additives were put, respectively, and cultured at 37° C. in an atmosphere of 5% $CO_2$ for 6 days, and the cell densities were measured. The experiment was carried out at n=2, and the average values were calculated. The results are shown in the following Table 1.

TABLE 1

| Additive | Solvent | Cell density (cells/ml) | Rate to control (%) |
|---|---|---|---|
| Gallic acid | Water | $1.48 \times 10^6$ | 171 |
| Salicylic acid | 50% Ethanol | $1.53 \times 10^6$ | 170 |
| m-Hydroxybenzoic acid | 50% Ethanol | $1.33 \times 10^6$ | 148 |
| Sodium m-hydroxybenzoate | Water | $1.30 \times 10^6$ | 150 |
| p-Hydroxybenzoic acid | 50% Ethanol | $1.56 \times 10^6$ | 173 |
| Sodium p-hydroxybenzoate | Water | $1.42 \times 10^6$ | 164 |
| m-Hydroxybenzaldehyde | 50% Ethanol | $1.22 \times 10^6$ | 136 |
| p-Hydroxybenzaldehyde | 50% Ethanol | $1.57 \times 10^6$ | 174 |
| Methyl p-hydroxybenzoate | Water | $1.41 \times 10^6$ | 163 |
| Ethyl p-hydroxybenzoate | Water | $1.05 \times 10^6$ | 121 |
| Water (control) | — | $8.65 \times 10^5$ | 100 |
| 50% Ethanol (control) | — | $9.00 \times 10^5$ | 100 |

Comparative Example 1

This experiment was carried out at the same time with the experiment of Example 1, under the same conditions as in Example 1, except that compounds analogous to the compounds of the formula (I) according to this invention shown in the following Table 2 were used as additives. The results are shown in Table 2.

TABLE 2

| Additive | Solvent | Cell density (cells/ml) | Rate to control (%) |
|---|---|---|---|
| Sodium benzoate | Water | $8.95 \times 10^5$ | 103 |
| m-Hydroxybenzyl alcohol | Water | $9.10 \times 10^5$ | 105 |
| p-Hydroxybenzyl alcohol | 100% Ethanol | $3.40 \times 10^5$ | 45 |
| p-Aminobenzoic acid | Water | $7.60 \times 10^5$ | 88 |
| Water (control) | — | $8.65 \times 10^5$ | 100 |
| 100% Ethanol (control) | — | $7.50 \times 10^5$ | 100 |

Example 2

Culture was carried out under the same conditions as in Example 1 except that portions of a 50% ethanol solution of methyl p-hydroxybenzoate (concentration: 10 mg/ml) were added, in place of the aqueous solutions or 50% ethanol solutions of additives in Example 1, so that the concentrations of methyl p-hydroxybenzoate in the media could be 0.04, 0.2, 1.0, 5.0 and 25 µg/ml, respectively. The results are shown in FIG. 1.

Example 3

1) Medium

As a basal medium was used a medium which comprises a medium comprising e-RDF having removed therefrom calcium salts other than calcium pantothenate (calcium chloride and calcium nitrate) (hereafter, referred to as low Ca e-RDF, calcium ion concentration 0.0026 mM), having added thereto calcium chloride in a concentration of 0.1 mM. To the basal medium were added as growth factors insulin, transferrin, ethanolamine and sodium selenite (ITES) in the respective concentrations of 9 µg/ml, 10 µg/ml, 10 µM and 20 nM. To the resultant medium was further added 5 µg/ml of methyl p-hydroxybenzoate as a 50% ethanol solution (concentration: 10 mg/ml).

2) Culture method and results

The resultant culture medium was fed into a culture vessel having a capacity of 300 ml previously autoclave sterilized, so that the net culture volume could be about 300 ml, and the 293 21-26 strain was seeded.

On the fourth day of culture were added 1.0 g of D-glucose and 32.6 mg of calcium chloride dihydrate as 3 ml of a mixed aqueous solution (the addition concentrations in the culture broth became 19 mM on glucose and 0.74 mM on calcium chloride).

Oxygen gas was introduced in the gaseous phase on the surface of the culture broth in the culture vessel while automatically controlled so that the concentration of dissolved oxygen could be 3 ppm.

The culture broth in the culture vessel was held at 37° C. A marine-type blade was installed in the culture vessel, and the stirring speed was made to be 40 rpm.

Figure 2:
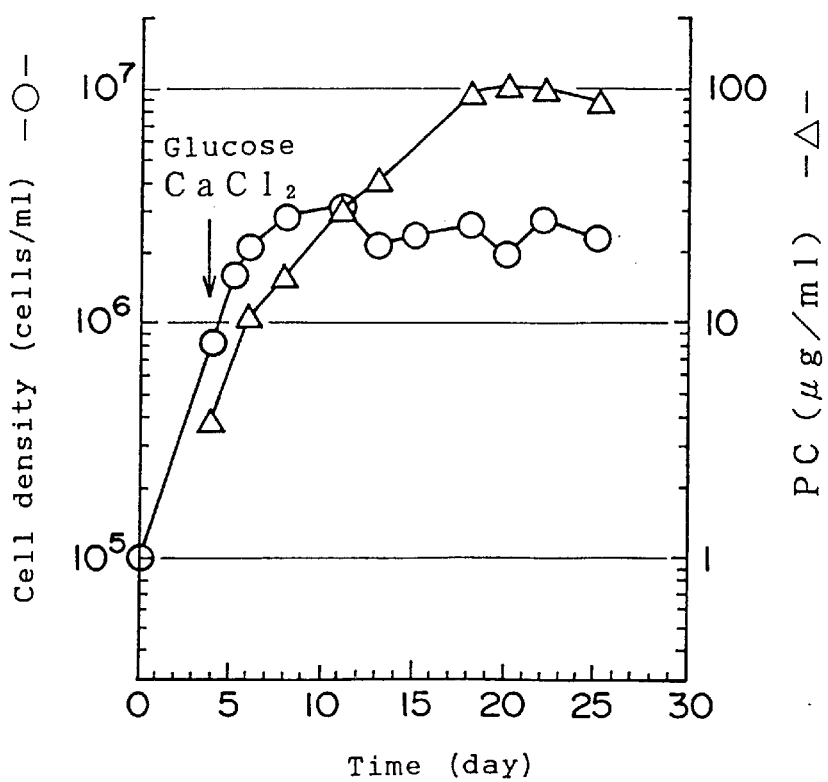
FIG. 2 is a graph showing the changes with time lapse of the cell density and the concentration of human protein C (PC) in the medium, obtained in Example 3.

The culture results are shown in FIG. 2. In FIG. 2, PC denotes protein C. This is also the case with FIGS. 3 to 5.

Comparative Example 2

Figure 3:
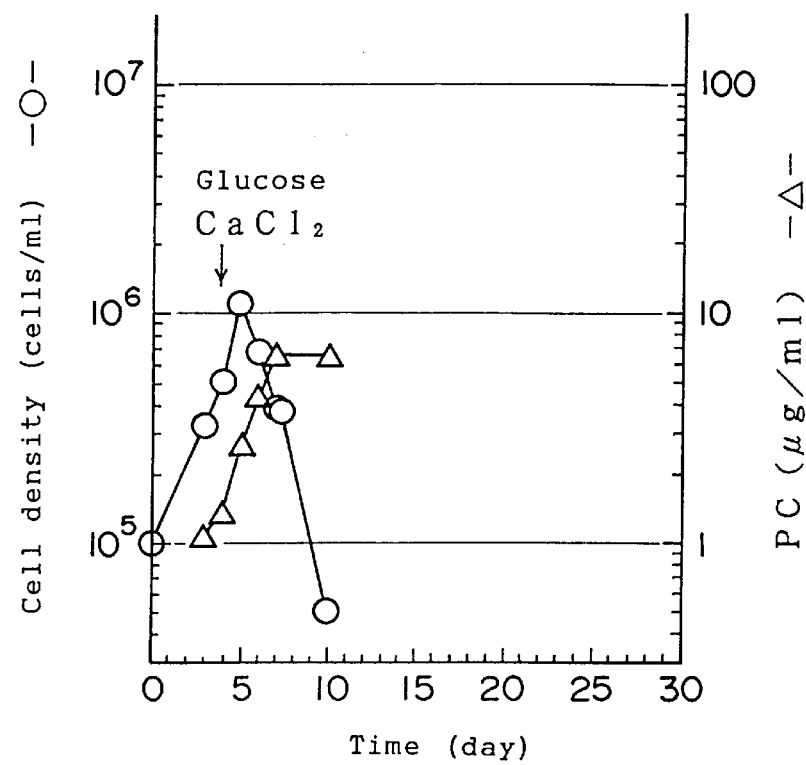
FIG. 3 is a graph showing the changes with time lapse of the cell density and the concentration of human protein C (PC) in the medium, obtained in Comparative example 2.

The same operations as in Example 3 were carried except that methyl p-hydroxybenzoate was not incorporated in the medium. The results are shown in FIG. 3.

Example 4

1) Medium

The same medium as in Example 3 was used except that fetal calf serum (FCS) was added so that the concentration could be 10% by weight, in place of ITES.

2) Culture method and results

Figure 4:
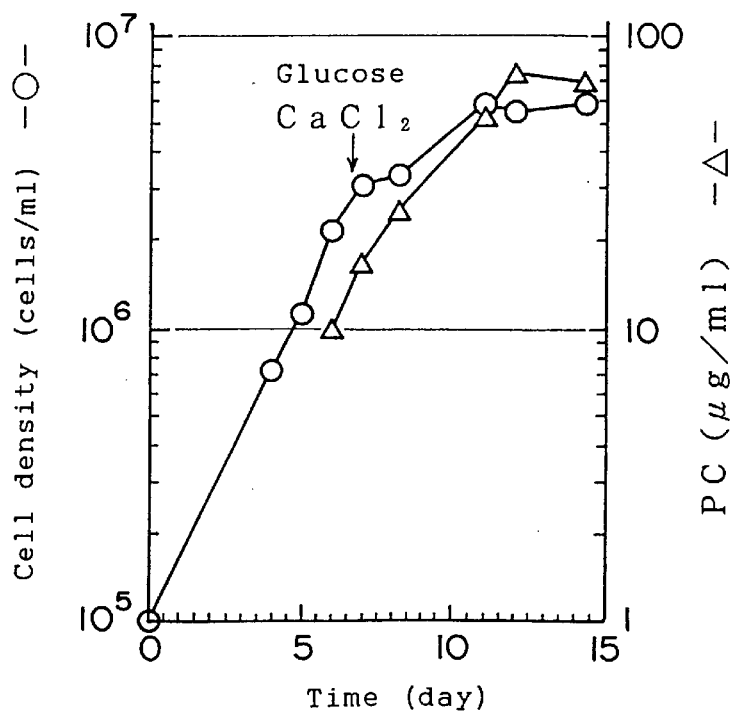
FIG. 4 is a graph showing the changes with time lapse of the cell density and the concentration of human protein C (PC) in the medium, obtained in Example 4.

Culture was carried out in the same manner as in Example 3 except that on the seventh day after the start of culture were added 1.0 g of D-glucose and 32.6 mg of calcium chloride dihydrate as 3 ml of a mixed aqueous solution (the addition concentrations in the culture broth became 19 mM on glucose and 0.74 mM on calcium chloride). The results are shown in FIG. 4.

Comparative Example 3

Figure 5:
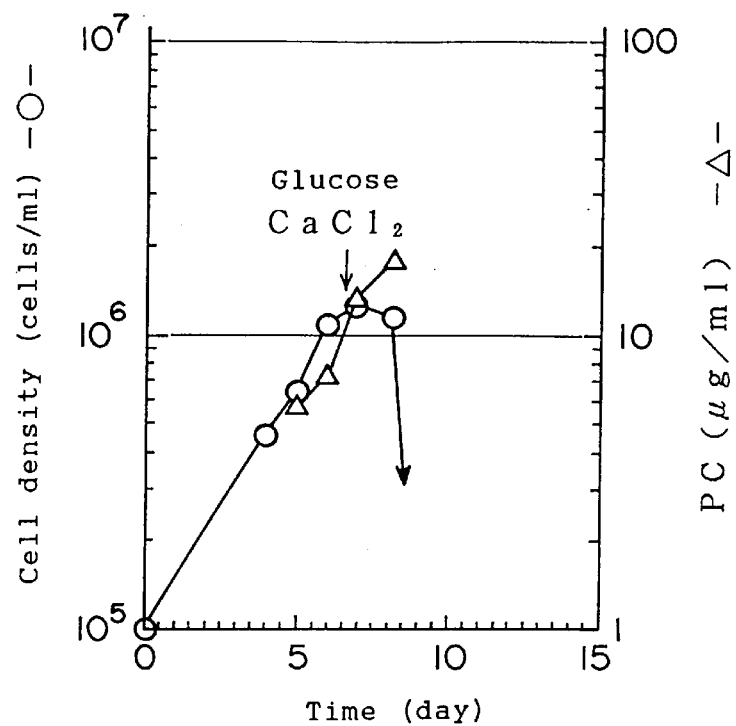
FIG. 5 is a graph showing the changes with time lapse of the cell density and the concentration of human protein C (PC) in the medium, obtained in Comparative example 3.

The same operations as in Example 4 were carried except that methyl p-hydroxybenzoate was not incorporated in the medium. The results are shown in FIG. 5. Almost all the cells died on the 9th day.

Example 5

1) Culture apparatus

Figure 7:
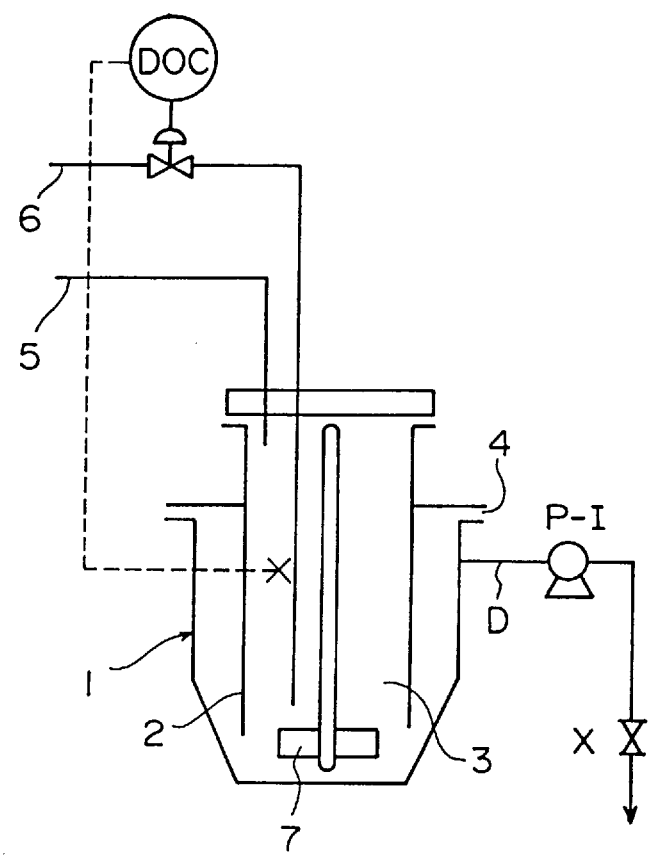
FIG. 7 is a schematic drawing of the culture system used in Example 5.

A culture system shown in FIG. 7 was used. As shown in FIG. 7, the culture vessel has a settling zone (3) partitioned by a bulkhead (2) inside the external wall (1), and an exhaust port (4) of the culture broth at the upper part, and the net culture capacity was about 120 ml.

2) Culture medium

ITES-e-RDF having the same composition as in Example 1, namely comprising e-RDF having added thereto ITES, was used. From the 7th day after the start of culture, the medium was changed to the same medium as above except for further containing 5 µg/ml of methyl p-hydroxybenzoate.

3) Culture method and results

The culture medium was fed into the above culture vessel previously autoclave sterilized through the line (5) so that the net culture volume could be about 120 ml, and to the medium was seeded a mouse×human hybridoma V3 strain (ATCC HB 9045) whose parent strain is a mouse myeloma cell P3U1 strain, so that the cell density could be $4.0 \times 10^6$ cells/ml. The cell is an IgG-producing strain. Oxygen gas was bubbled into the culture vessel through the line (6) while automatically controlled by DOC (dissolved oxygen-controlling apparatus) so that dissolved oxygen in the medium could be 3 ppm. The temperature of the culture broth in the culture vessel was held at 37° C. A marine-type blade (7) was installed in the culture vessel, and stirred at a stirring speed of 40 rpm.

Perfusion was started immediately after the seeding. The rate of perfusion was such that the substitution rate per day of the net culture volume could be twice.

Figure 6:
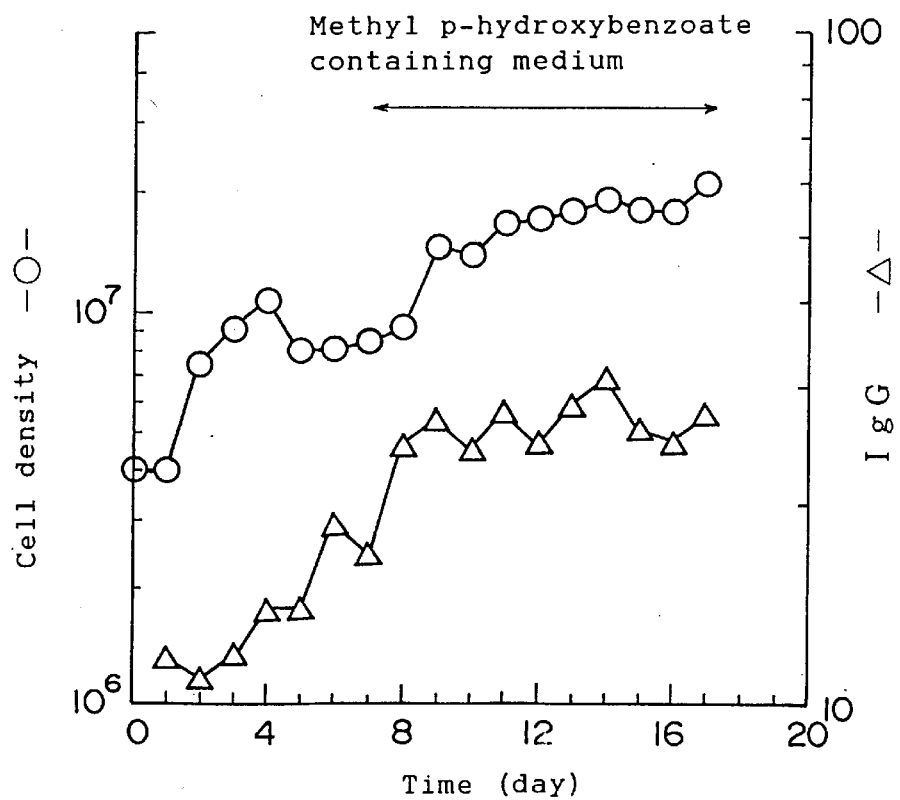
FIG. 6 is a graph showing the changes with time lapse of the cell density and the concentration in the medium of IgG produced by the mouse×human hybridoma V3 strain, obtained in Example 5.

The above culture operations were continued for 17 days. The results are shown in FIG. 6.

Example 6

1) Medium

The same medium as in Example 3 was used.

2) Culture method and results

The medium was fed into a culture vessel having a capacity of 1.4 L previously autoclave sterilized, so that the net culture volume could be about 700 ml, and to the medium was seeded the 293 21-26 strain.

On the first day after the start of culture, the medium was additionally fed so that the net culture volume in the culture vessel could be about 1.4 L.

Feeding of oxygen gas into the culture vessel was not made for 4 days after the start of culture, and thereafter, the feeding amount was automatically controlled using pure oxygen gas so that the concentration of dissolved oxygen could be 2 to 3 ppm. Oxygen gas was fed into the culture broth through a porous silicone tube. Control of the pH was not made at all.

The temperature of the culture broth in the culture vessel was held at 37° C. A marine-type blade was installed in the culture vessel, and stirred at a stirring speed of 25 rpm.

On the sixth day after the start of culture, 1.0 g of D-glucose and 152.1 mg of calcium chloride dihydrate were added as 14 ml of a mixed aqueous solution (the final addition concentrations in the culture broth became 19 mM on glucose and 0.74 mM on calcium chloride).

Figure 8:
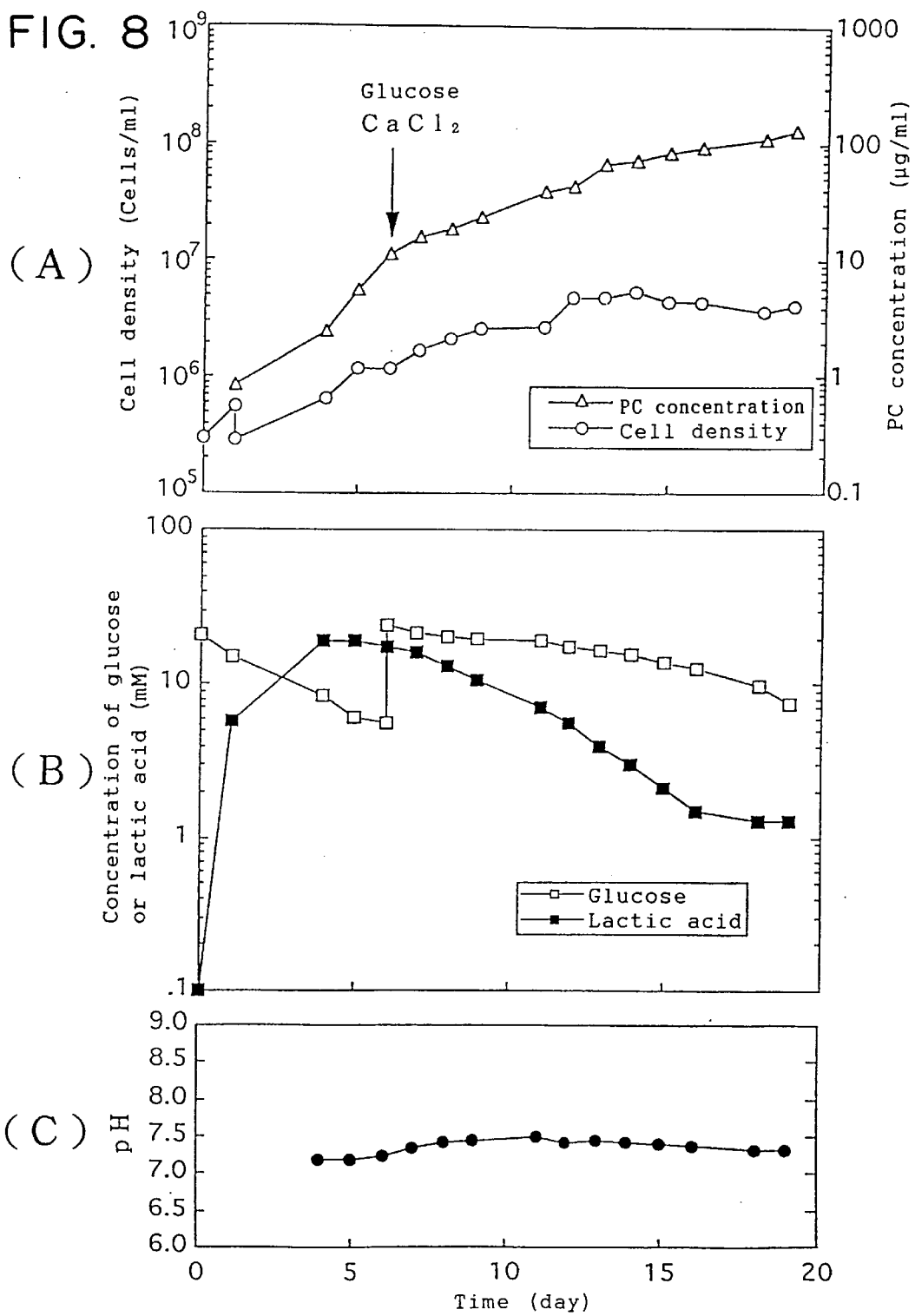
In FIG. 8, (A) is a graph showing the changes with time lapse of the cell density and the concentration in the medium of human protein C (PC), obtained in Example 6, (B) is a graph showing the changes with time lapse of the concentrations in the medium of glucose and lactic acid, and (C) is a graph showing the change with time lapse of the pH of the medium.

The culture results are shown in FIG. 8. In FIG. 8, (A) is the results of assay of the cell density and the PC concentration in the culture broth, (B) is the results of measurement of the glucose concentration and the lactic acid concentration, and (C) is the results of measurement of the pH of the medium. As shown in FIG. 8 (B), from about the time when feeding of oxygen gas was started, decrease of lactic acid was observed although plenty of glucose was present. Further, as shown in FIG. 8 (C), the pH scarcely changed during the culture.

Example 7

1) Medium

The same ITES-e-RDF medium as in Example 1 was prepared, and methyl p-hydroxybenzoate was added to the medium as a 50% ethanol solution (concentration: 10 mg/ml) so that the concentration could be 5 μg/ml.

2) Cell

The 293 cell (ATCC CRL-1573) derived from a human fetal kidney cell, which was obtained from ATCC, was used.

3) Culture method and results 3 ml portions of a suspension of the 293 cell in the medium at a density of $3\times10^4$ cells/ml were put in 35 mmφ plastic dishes for animal cells, respectively, and cultured at 37° C. in an atmosphere of 5% $CO_2$ for 8 days. The experiment was carried out at n=3. The results are as shown in Table 3, and the cell density in the case of addition of methyl p-hydroxybenzoate was 157% higher than that in the control.

TABLE 3

| Additive | Cell density* (cells/ml) | Rate to control (%) |
|---|---|---|
| Methyl p-hydroxybenzoate | $3.53 \times 10^5$ | 157 |
| No addition (control) | $2.25 \times 10^5$ | 100 |

*Average value based on three times experiments

Example 8

1) Medium

The same ITES-e-RDF medium as in Example 1 was prepared, and methyl p-hydroxybenzoate was added to the medium as a 50% ethanol solution (concentration: 10 mg/ml) so that the concentration could be 5 μg/ml.

2) Cell

The HepG2 cell (ATCC HB-8065) derived from a human hepatoma, which was obtained from ATCC, was used.

3) Culture method and results 4 ml portions of a suspension of the HepG2 cell in the medium at a density of $1\times10^6$ cells/ml were put in 35 mmφ plastic dishes for animal cells, respectively, and cultured at 37° C. in an atmosphere of 5% $CO_2$ for 4 days. The results are as shown in Table 4, and the cell density in the case of addition of methyl p-hydroxybenzoate was 123% higher than that in the control.

TABLE 4

| Additive | Cell density (cells/ml) | Rate to control (%) |
|---|---|---|
| Methyl p-hydroxybenzoate | $2.31 \times 10^5$ | 123 |
| No addition (control) | $1.87 \times 10^5$ | 100 |

Example 9

1) Culture apparatus

An apparatus was used which has the same type as that used in Example 5 and has a net culture volume of about 200 ml.

2) Culture medium

The same ITES-eRDF as in Example 1 containing 5 μg/ml of methyl p-hydroxybenzoate was used.

3) Cell

The BHK-12D strain disclosed in Japanese Laid-Open Patent Publication No. 71484/1992, which is derived from the BHK-21 strain (ATCC CCL-10) obtained from ATCC, was used.

4) Culture method and results

The same operations as in Example 5 were carried out except that the seeding density was made to be $1\times10^5$ cells/ml, the net culture volume was made to be 200 ml, and the perfusion rate was made to be once per day up to the second day and twice per day after the second day. Culturing was continued for 9 days. The results are shown in FIG. 9 (*a*).

Comparative Example 4

The same operations as in Example 9 were carried out except that methyl p-hydroxybenzoate was not incorporated in the medium. The results are shown in FIG. 9 (b).

Example 10

Activated protein C (APC) was prepared from the culture broth obtained in Example 1 according to the following procedure.

(1) Purification of recombinant protein C (rPC)

The pH of about 500 ml of the culture supernatant of the rPC-producing cell having a rPC concentration of 37 µg/ml was adjusted so as to be in the range of 7.2 to 7.4, and 1M $CaCl_2$ was added so that the final concentration could be 5 mM. The supernatant was filtered using a filter 0.45 µm thick, and the filtrate was applied onto a column of immobilized anti-PC monoclonal antibody. This column was obtained by immobilizing $Ca^2$-dependent human PC monoclonal antibody: JTC-1 (see Journal of Biological Chemistry 261, 24, 11097, 1986) on Formyl-Cellulo Fine Gel (Seikagaku Kogyo Co.) in the rate of 4 mg IgG/ml gel, and packing 10 ml of the resultant gel into a glass column, and used after equilibrated by flowing an equilibrating buffer of 0.05M Tris/HCl, 0.15M NaCl and 5 mM $CaCl_2$ (pH 7.4).

After the sample application, the column was washed with 10 to 20 times the column volume of a washing buffer of 0.05M Tris/HCl, 1.0M NaCl and 5 mM $CaCl_2$ (pH 7.4), it was confirmed that the absorbance of the eluate at 280 nm was sufficiently lowered, and then rPC bound to the immobilized antibody was eluted with an eluent of 0.05M Tris/HCl, 0.15M NaCl and 10 mM EDTA (pH 7.4). The eluted PC fractions were dialyzed against 0.05M Tris/HCl and 0.15M NaCl (pH 7.4) (TBS), and then concentrated so that the PC concentration could be 2 mg/ml. By the above operations, about 11 mg of rPC was obtained from 500 ml of the supernatant.

(2) Activation and separation of APC 280 units of bovine thrombin (Mochida) and 1 mM as the final concentration of EDTA were added to 3.7 mg of purified rPC, TBS was added to make the whole amount 3 ml, and the mixture was subjected to reaction at 37° C. for 3 hours. After the reaction, 3 ml of 0.02M MES/Tris and 0.1M NaCl (pH 6.0) was added, the pH was adjusted to 6.0 by (or with) 1M MES, and then the mixture was applied onto an S-Sepharose (Pharmacia) column (1.5 cm×4 cm) equilibrated with 0.02M MES/Tris and 0.1M NaCl (pH 6.0).

After the application, elution was carried out by a linear gradient of NaCl 0.1M→1.0M. In this operation, the APC peak was eluted prior to the thrombin peak. Eluted fractions were taken out from the 41st to 49th tubes (1 ml/tube), concentrated using an ultrafiltration membrane (Amicon YM 10), and dialized against TBS. About 2 mg of rAPC was finally obtained.

(3) Assay of rAPC activity

The activity of APC was evaluated by assay of APTT with addition of APC. 100 µl of rAPC diluted with TBS containing 0.1% BSA, and Actin (Dade) were added to 100 µl of normal human plasma (Dade, Ci-trol I) warmed at 37° C. for one minute, the mixture was subjected to incubation at 37° C. for 2 minutes, 100 µl of 25 mM $CaCl_2$ was added, and then the coagulation time was measured using a blood coagulation time measuring apparatus (CA-100) of Sysmex Co.

Figure 10:
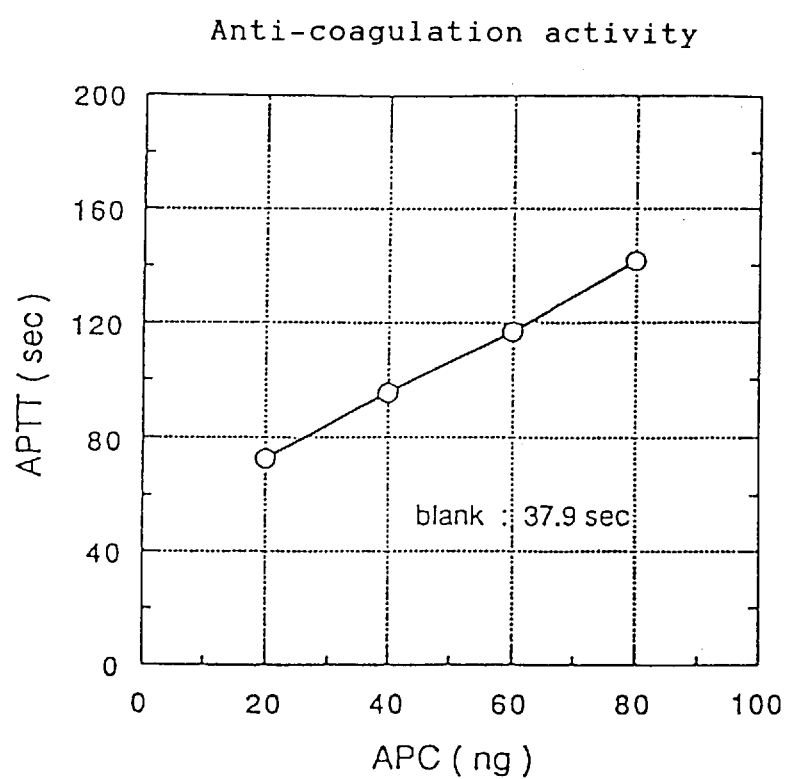
FIG. 10 is a graph showing the relation between the addition amount of activated protein C (APC) and the coagulation time (ATPP), obtained in Example 10.

By addition of APC, volume-dependent extension of APTT was observed in the range of 20 to 80 ng, and this action was almost the same as in plasma-derived APC (FIG. 10).

Thus, it was shown that rAPC prepared from rPC produced according to the culture method of this invention has an activity equal to that of plasma-derived APC.

---

We claim:

1. A cell culture medium for culturing animal cells which contains a compound represented by the general formula

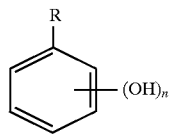
(I)

wherein, R denotes COOM or CHO, herein M denotes hydrogen, an alkali metal or a $C_1$ to $C_3$ alkyl group, and n is an integer of 1 to 3.

2. The medium according to claim 1 wherein said compound of the formula (I) is selected from the group consisting of

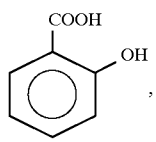,

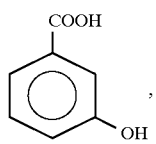,

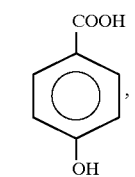,

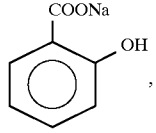,

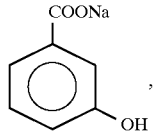,

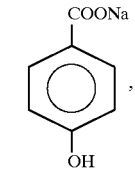,

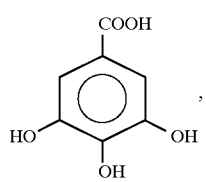,

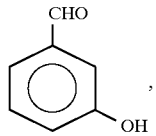,

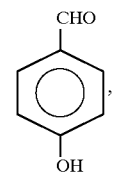,

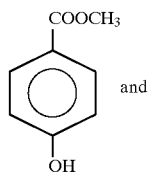 and

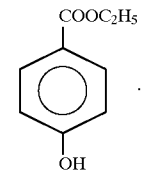.

3. The medium according to claim 1 wherein said medium contains the compound of the formula (I) at a concentration of 0.05 to 50 μg/ml.

4. The medium according to claim 1 wherein said medium contains the compound of the formula (I) at a concentration of 0.2 to 20 μg/ml.

5. The medium according to claim 1 wherein said animal cell is a tumor cell or a fetus-derived cell.

6. The medium according to claim 1 wherein said animal cell is an animal cell of an animal cell line.

7. The medium according to claim 1 wherein said animal cell is an animal cell of a human fetal kidney 293 strain or a transformant thereof.

8. The medium according to claim 1 wherein said animal cell is an antibody-producing hybridoma.

9. The medium according to claim 1 wherein said animal cell is a human hepatoma-derived established cell.

10. The medium according to claim 1 wherein said medium is a medium containing 2,000 to 5,000 mg/l glucose.

11. A medium composition for culture of animal cells containing nutrients necessary for proliferation of the animal cells, and a compound represented by the general formula

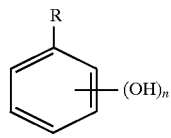
(I)

wherein, R denotes COOM or CHO, herein M denotes hydrogen, an alkali metal or a $C_1$, to $C_3$ alkyl group, and n is an integer of 1 to 3.

12. A method for obtaining a useful protein by culturing protein-producing animal cells in a medium, recovering the produced protein from the culture broth, and, if necessary further treating the protein, characterized in that said medium contains a compound represented by the general formula

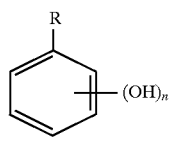 (I)

wherein, R denotes COOM or CHO, herein M denotes hydrogen, an alkali metal or a $C_1$ to $C_3$ alkyl group, and n is an integer of 1 to 3, and said protein-producing animal cell is human fetal kidney-derived 293 strain transformed with a recombinant expression vector containing a gene encoding a Gla protein.

13. The method according to claim 12 wherein said Gla protein is human protein C or activated human protein C.

14. The method according to claim 12 wherein said Gla protein is human protein C, and which contains a step of enzyme treating human protein C recovered from the culture broth to give an activated peptide.

* * * * *